United States Patent [19]

Doerr

[11] Patent Number: 4,620,032

[45] Date of Patent: Oct. 28, 1986

[54] DEPOLYMERIZATION OF CONDENSATION POLYMERS INVOLVING A PRE-MOLECULAR WEIGHT REDUCTION STEP

[75] Inventor: Marvin L. Doerr, Charlotte, N.C.

[73] Assignee: Celanese Corporation, New York, N.Y.

[21] Appl. No.: 680,443

[22] Filed: Dec. 11, 1984

[51] Int. Cl.$^4$ .................. C07C 51/487; C07C 99/12; C07C 27/26; C07C 85/26

[52] U.S. Cl. .................. 562/483; 562/485; 562/487; 562/458; 562/554; 562/590; 562/593; 564/498; 568/858

[58] Field of Search .............. 562/483, 485, 487, 458, 562/554, 590, 593; 568/858; 564/498

[56] References Cited

U.S. PATENT DOCUMENTS 3,488,298  1/1970  Barkley et al. .................. 562/485

*Primary Examiner*—Natalie Trousof
*Assistant Examiner*—Vera C. Clarke
*Attorney, Agent, or Firm*—Forrest D. Stine

[57] ABSTRACT

There is disclosed a process for reducing the reaction time in the hydrolysis of a condensation polymer wherein molten condensation polymer is intimately admixed with a depolymerizing agent which is either (i) one of the products resulting from the complete hydrolytic depolymerization of the condensation polymer; or (ii) water. The depolymerization agent is present in the mixture in an amount which is less than the weight of the condensation polymer and the materials are intimately admixed for a time sufficient that the molecular of the condensation polymer is reduced by at least 50%. The treated condensation polymer of lower molecular weight is thereafter subjected to neutral hydrolysis. In addition to decreasing the overall time required to effect complete hydrolytic depolymerization, this process additionally permits the use of a smaller hydrolysis vessel, thereby reducing the fabrication cost of the hydrolysis unit.

25 Claims, 2 Drawing Figures

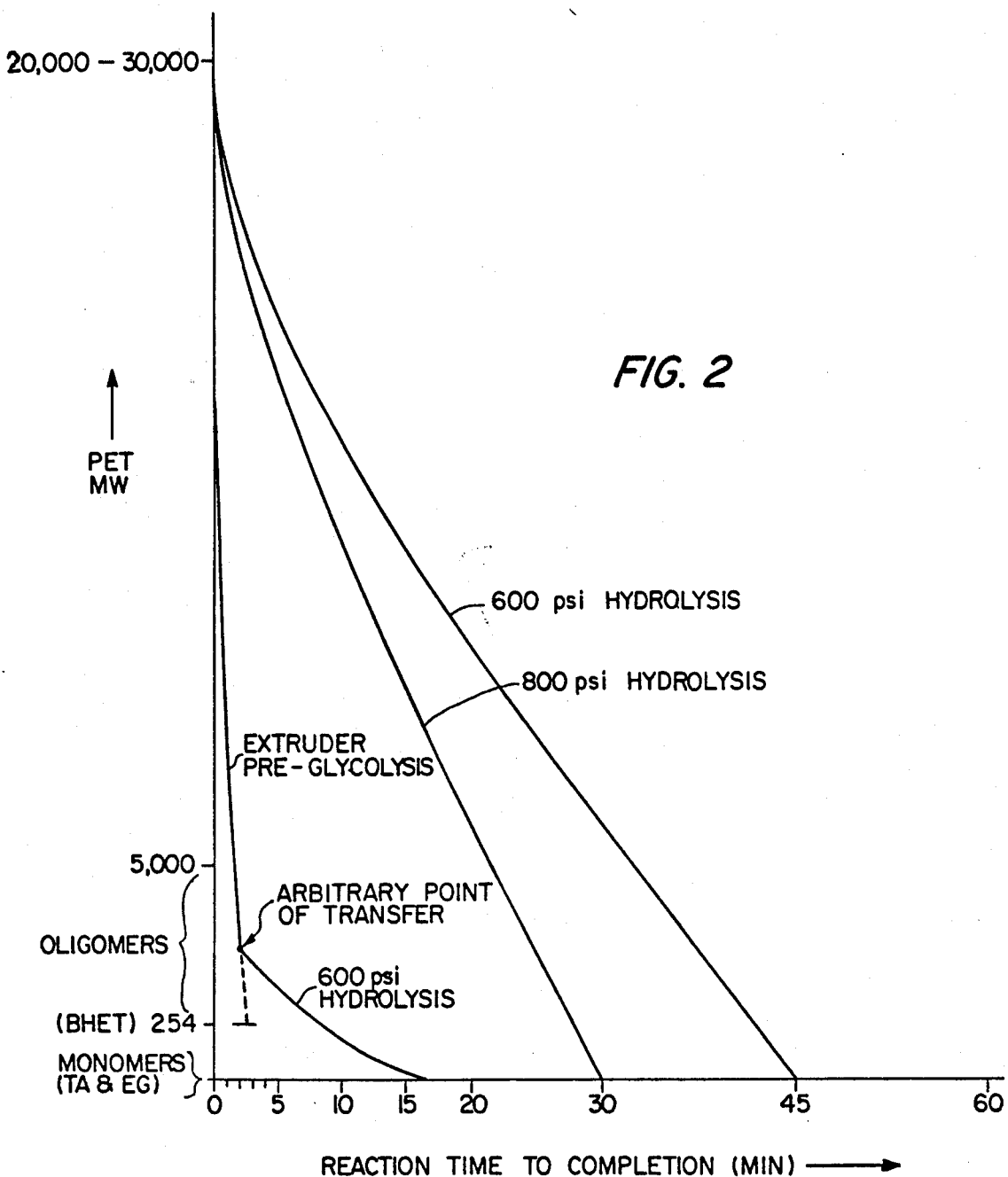

DEPOLYMERIZATION OF CONDENSATION POLYMERS INVOLVING A PRE-MOLECULAR WEIGHT REDUCTION STEP

BACKGROUND OF THE INVENTION

The invention relates a process for depolymerizing condensation polymers. More specifically, the invention is directed to a process for depolymerizing condensation polymers in which a condensation polymer is subjected to a pre-molecular weight reduction step and thereafter subjected to neutral hydrolysis.

The continuous hydrolysis of high molecular weight condensation polymers including polyesters such as polyethylene terephthalate, polyamides such as nylon 6 and nylon 66 and polycarbonates has been disclosed in the art by references including Canadian Pat. No. 611,032 to Katzschmann; Japanese SHO No. 49 [1974]-76968 to Tanaka et al; and in co-pending U.S. application Ser. No. 563,812, filed Dec. 21, 1983. These processes involve treating a condensation polymer, including oligomeric waste, with a substantial excess of water under conditions of high temperature and pressure and result in the reversal of polycondensation. For example, terephthalic acid and ethylene glycol are the primary products of polyethylene terephthalate hydrolysis.

Under optimum hydrolysis conditions of high pressure, high temperature and high polymer concentration, depolymerization products such as terephthalate acid, exhibit a high degree of corrosiveness on reactor components. Thus, in those parts of the reaction vessels that are exposed to extreme conditions, expensive acid-resistant metals are preferred, e.g., titanium, Hastaloys, Carpenter Stainless and the like. To minimize the cost of these parts, in particular the hydrolyzer vessel itself, a small vessel is preferred. Since smaller vessels dictate high throughputs of feed material, processes have been sought to minimize residence time of the condensation polymer in the hydrolyzer but which nevertheless effect substantially complete depolymerization, e.g., of polyethylene terephthalate to terephthalic acid and ethylene glycol.

Several factors are believed to govern the rate of hydrolysis. These include pressure (or temperature) in the hydrolyzer, surface-to-volume ratio of the condensation polymer feed materials, the degree of crystallinity of the polymer feed material, and the molecular weight of the polymer feed material. Hydrolysis rates may be increased, resulting in reduced residence by: (1) increasing pressure (or temperature); (2) increasing the surface to volume ratio of the feed material; (3) decreasing the degree of crystallinity of the feed material; or (4) decreasing the molecular weight of the feed material. In actual practice, there are practical ceilings of operation. Pressure is limited by equipment duty, availability and safety. Surface/volume ratios and degrees of crystallization are usually fixed prior to hydrolysis by the physical form and nature of the polymer, e.g., polyethylene terephthalate, being feed. Thus, the artisan is faced with a limited degree of flexibility in modifying hydrolysis processes to increase reaction rate within the hydrolyzer.

SUMMARY OF THE INVENTION

A process has now been found for reducing the reaction time in the hydrolysis of a condensation polymer. In accordance with the invention, molten condensation polymer is intimately admixed with a depolymerizing agent which is either (i) one of the products resulting from the complete hydrolytic depolymerization of the condensation polymer; or (ii) water. The depolymerization agent is present in the mixture in an amount by weight which is less than the weight of the condensation polymer. The molten condensation polymer and the depolymerization agent are admixed intimately for a time sufficient that the molecular weight of the condensation polymer is reduced by at least fifty percent. Thereupon, the treated condensation polymer is subjected to neutral hydrolysis with a substantial excess of water, based on the weight of the treated condensation polymer, to thereby effect substantially complete hydrolytic depolymerization of the condensation polymer. In preferred embodiments of the invention, the molten condensation polymer and the depolymerizing agent are intimately admixed in a weight ratio of at least about 10:1 in a high temperature, high pressure screw extruder which is operated at a pressure greater than or equal the pressure in the hydrolysis zone. In addition to decreasing the overall time required to effect complete hydrolytic depolymerization of a condensation polymer, the process of the invention additionally permits the use of a smaller hydrolysis vessel, thereby reducing the fabrication cost of the hydrolysis unit.

BRIEF DESCRIPTION OF THE DRAWINGS

In the drawings which form part of the original disclosure of the invention:

FIG. 2 is a graph illustrating a comparison of the time required for complete hydrolytic depolymerization of a condensation polymer in accordance with the invention, with the time required for complete hydrolytic depolymerization of a condensation polymer at different conditions wherein a pre-molecular weight reduction step is not used.

DETAILED DESCRIPTION OF THE INVENTION

Figure 1:
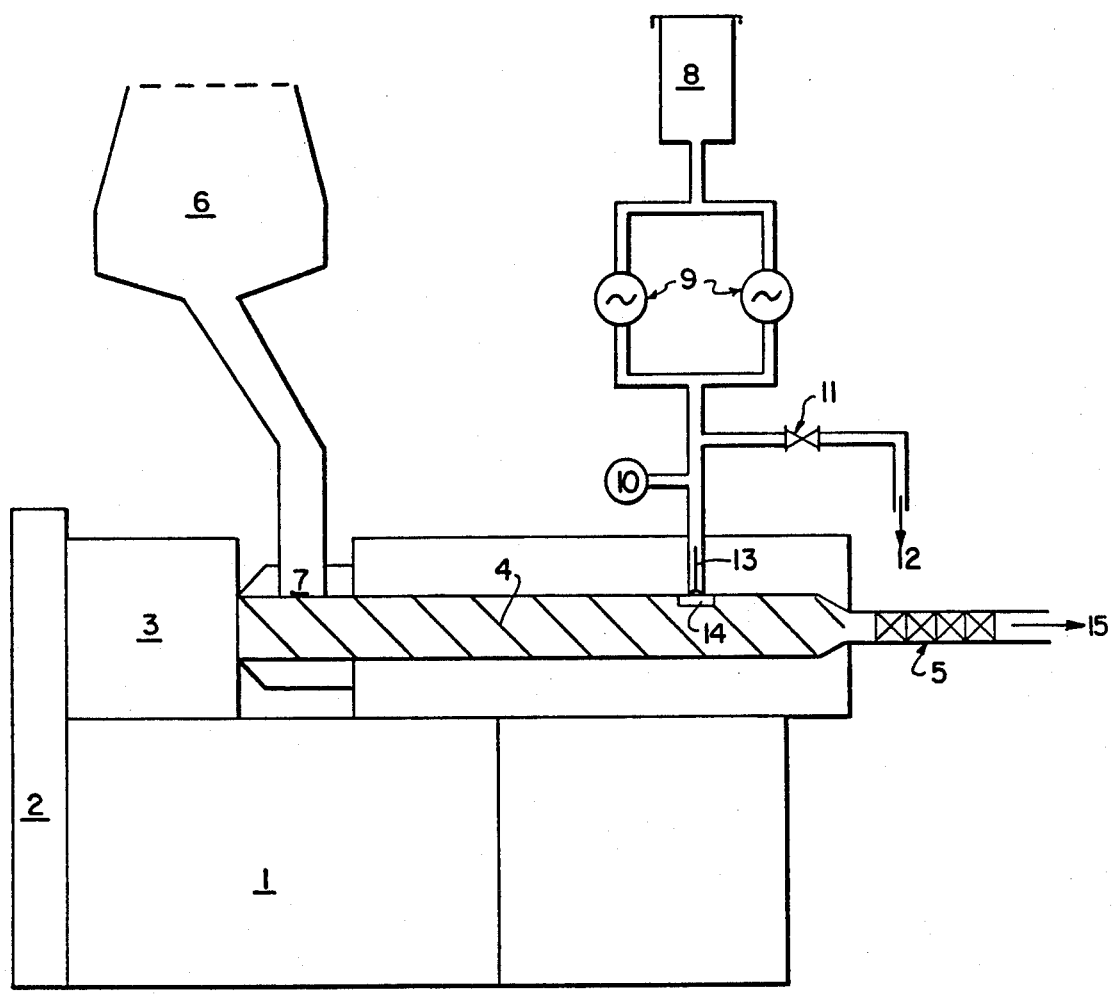
FIG. 1 is a schematic view partially in section of an apparatus for accomplishing the pre-molecular weight reduction step in one embodiment of the invention.

Condensation polymers which may be treated for reduction of molecular weight and thereafter hydrolyzed in accordance with the invention are well known in the art and do not per se constitute a part of this invention. Examples of condensation polymers include polyesters obtained by the condensation of a dicarboxylic acid and a dihydric alcohol and characterized by repeating units of the following formula:

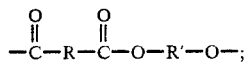

polyamides obtained by the condensation of a dicarboxylic acid and an alkylene diamine or by the head to tail condensation of an amino carboxylic acid or the corresponding lactam and characterized by the structural formulas:

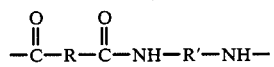

and

-continued

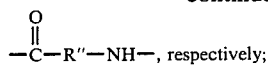

and polycarbonates obtained by the reaction of phosgene and a dihydric phenol and characterized by repeating units having the structure

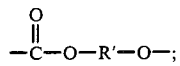

wherein, R, R' and R" are divalent organic radicals. Exemplary condensation polymers which may be treated in accordance with the invention include polyethylene terephthalate, polybutylene terephthalate, nylon 6 and nylon 66.

Condensation polymer materials which may be treated in accordance with the invention may be in various physical forms including waste material resulting from the manufacture of articles from the condensation polymers, e.g., waste material which is produced during the production of polymer, fibers, chip, film, molded articles such as bottles or the like. The condensation polymer may be oligomeric in nature and as used herein, the term "condensation polymer" is meant to include such materials. The condensation polymer may also be in the form of finished articles, e.g., molded bottles, from which it is desired to reclaim the starting monomers. The condensation polymer material is supplied to the pre-molecular weight reduction zone in the form of granules or yarns or as a viscous liquid or in some other form suitable for handling. The polycondensation polymer should be liquid, i.e., molten, under the conditions of temperature and pressure of the pre-molecular weight reduction zone. Advantageously the temperature in the pre-molecular weight reduction zone will be greater than the melting temperature of the polymer at atmospheric pressure, more advantageously at least 10° C. higher than the polymer melting temperature even more advantageously, at least 20° C. greater than the melting temperature.

The depolymerizing agent, i.e., water or depolymerization product, used to treat the condensation polymer to reduce the molecular weight thereof should also be liquid under the conditions of pressure and temperature existing in the pre-molecular weight reduction zone. The depolymerizing agent is intimately admixed with the condensation polymer in an amount which is less, by weight, than the polymer weight. Advantageously the amount of depolymerizing agent used is less than 50% of the polymer weight; more advantageously, the depolymerizing agent is used in an amount which is less than about 25% by weight, even more advantageously, an amount which is less than about 10% by weight, most advantageously an amount which is less than about 5% by weight, based on the polymer weight. Surprising such small amounts of depolymerizing agent can, under proper temperature, pressure, and conditions of intimate admixing, both rapidly and drastically reduce the molecular weight of the polymer.

Preferably, the molecular weight reduction treatment is accomplished in a screw-type extruder. The screw extruder, which is advantageously of the high temperature and high pressure type, accomplishes intimate admixing of the depolymerizing agent and the molten polymer. Because of the high temperature and pressure and high shear mixing in the extruder, the admixture of polymer and depolymerizing agent forms a substantially homogeneous mass with the result that molecular weight reduction can be extremely rapid, e.g., molecular weight reduction can be substantially complete in less than 2 minutes. The extruder, in turn, feeds the condensation polymer of reduced molecular weight in a continuous manner, to the hydrolyzer. Alternatively, the waste material can be melted and mixed with the molecular weight reducing agent and injected continuously into the hydrolyzer by means of a high-pressure pump.

As previously mentioned, the temperature and pressure conditions in the pre-molecular weight reduction zone are such that the condensation polymer is molten. Additionally, the pressure must be higher than the vapor pressure of the pre-molecular weight reducing agent at the particular temperature conditions existing in the zone. Furthermore, the pressure in the pre-molecular weight reduction zone is preferably equal to or greater than the pressure of the hydrolytic depolymerization zone.

In a preferred embodiment, the condensation polymer is polyethylene terephthalate and the depolymerizing agent is ethylene glycol. Ethylene glycol is injected into the molten polyethylene terephthalate to reduce its molecular weight. Such a process is referred to herein as "pre-glycolysis". When coupled with a hydrolyzer vessel, the overall rate of the depolymerization is faster, i.e., reduced residence time is required, than either process for depolymerization if employed separately. Thus, if polyethylene terephthalate is continuously fed by means of a melt extruder to a hydrolyzer operating at 600 psi and containing a substantial excess of water, the required equilibrium residence time to insure a complete reaction from polyethylene terephthalate to terephthalic acid and ethylene glycol is on the order of 45 minutes. In contrast, the reaction time in a hydrolyzer from low molecular weight polyethylene terephthalate oligomers to terephthalic acid and ethylene glycol in on the order of 12 to 15 minutes. Further, when polyethylene terephthalate is subjected to an isolated pre-glycolysis reaction in which ethylene glycol is metered into melted polyethylene terephthalate while in a melt extruder, molecular weight reduction takes place extremely rapidly, i.e., in less than two minutes, above the melting point of polyethylene terephthalate. However, the resultant products are not terephthalic acid and ethylene glycol, but rather bis-2-hydroxyethyl terephthalate (BHET), a low melting polyester oligomer plus a variety of other hydroxyl-terminated oligomers. No matter how long the residence time, no terephthalic acid or ethylene glycol are formed during the pre-glycolysis reaction. However, when both the pre-glycolysis and hydrolysis processes are coupled in series, then the net result is the formation of the desired end products, i.e., terephthalic acid and ethylene glycol, in from one-third to one-half the residence time of hydrolysis, alone.

Theoretically, terephthalic acid could be substituted for ethylene glycol in the condensation polymer pre-molecular weight reduction process. However, terephthalic acid is a solid that exhibits no melting point. Therefore, its use is somewhat more complicated and less efficient than ethylene glycol which is a liquid.

It is preferred not to have water present during the molecular weight reduction process of polyethylene terephthalate since water reacts with polyethylene terephthalate to give carboxy-terminated oligomers that exhibit high melting points, frequently higher than the melting point of the molten polyethylene terephthalate. However, with other condensation polymers, the use of water will not produce undesirable intermediate oligomers and can readily be used.

Extruder conditions suitable to the pre-glycolysis of polyethylene terephthalate are 260°–310° C., preferably 280°–290° C., at pressures of 500–2,000 psi. To facilitate transfer of the feed material from the extruder, it is preferred that the extruder be operated at a pressure not less than that of the hydrolyzer.

In the preferred extruder arrangement, the molecular weight reducing chemical, e.g., ethylene glycol, is metered via a single or multiplexed piston pump, through a spring-loaded valve situated such that its outlet discharges into the barrel of the extruder. It is also preferred to have a static mixer in-line down-stream of the point of injection prior to entrance into the hydrolyzer vessel.

The molecular weight reducing zone is operated to reduce the molecular weight of the condensation polymer by at least 50 percent. The amount added, or addition rate, of the molecular weight reducing chemical is only a function of the initial and desired final molecular weight, or intrinsic viscosity (IV), of the feed condensation polymer and final product. This is defined by the following equation:

$$\left[\begin{array}{c}\text{Depolymerizing Agent}\\\text{Addition Rate}\end{array}\right] = \frac{\left[\begin{array}{c}\text{Depolymerizing}\\\text{Agent}\\\text{Molecular}\\\text{Weight}\end{array}\right]\left[\begin{array}{c}\text{Condensation}\\\text{Polymer}\\\text{Throughput}\\\text{Rate}\end{array}\right][(M_o/M_f) - 1]}{M_o}$$

where $M_o$ = Initial molecular weight of Polymer feed (or more accurately, of the polymer extrudate without addition of a molecular weight reducing chemical)

$M_f$ = Desired final molecular weight of extrudate

Using ethylene glycol (EG) as the molecular weight reducing chemical and polyethylene terephthalate (PET) as the polymer, this becomes:

$$\frac{\text{EG}}{\text{Addition Rate}} = \frac{(62)(\text{PET Throughput Rate})[(M_o/M_f) - 1]}{M_o}$$

To convert polyethylene terephthalate molecular weights to intrinsic viscosities (IV's), the following Mark-Houwink equation can be used as a good estimate:

$$M = 3.486 \times 10^4 \, (IV)^{1.205}$$

As predictive examples showing that relatively small amounts of molecular weight reducing chemical are required to be added to effect reduction the polyethylene terephthalate molecular weight, the following table is provided at two initial molecular weights (IV's):

| Wt % EG | Initial Extruded $M_o$ (IV$_o$) = 30,000 (0.89) Final M$_f$* (IV$_f$) | Initial Extruded $M_o$ (IV$_o$) = 20,000 (0.63) Final M$_f$* (IV$_f$) |
| --- | --- | --- |
| 0 | 30,000 (0.89) | 20,000 (0.63) |
| 0.5 | 8,775 (0.32) | 7,655 (0.28) |
| 1.0 | 5,140 (0.20) | 4,735 (0.19) |
| 1.5 | 3,635 (0.15) | 3,425 (0.15) |
| 2.0 | 2,810 (0.12) | 2,685 (0.12) |
| 3.0 | 1,935 (0.1) | 1,875 (0.1) |
| 4.0 | 1,475 (n/a) | 1,440 (n/a) |
| 5.0 | 1,190 (n/a) | 1,170 (n/a) |
| 10.0 | 605 (n/a) | 600 (n/a) |

*Calculated from: $M_f = \dfrac{6200 \, (M_o)}{(\text{Wt \% EG})(M_o) + 6200}$

Actual experiments were performed from about 30,000 molecular weight PET with 0 to 2.53 wt % EG with excellent agreement of actual final $M_f$ to the predicted $M_f$.

The following examples illustrate the invention:

EXAMPLE 1

In this embodiment, the method of the invention is carried out with the equipment illustrated in FIG. 1. In this Figure, there is shown an extruder motor 1, a drive 2 and a transmission 3 which drives the extruder screw 4 which is in communication with an in-line static mixer 5. Polyethylene terephthalate is fed from the polymer feed hopper 6 through the polymer feed inlet 7 into the extruder where it is melted. Ethylene glycol is fed from the pre-molecular weight reduction additive reservoir 8 by means of duplexed piston pumps 9 to the extruder. There is provided a pressure gauge 10 and a pressure relief valve 11 which permits excess ethylene glycol to be passed out of the system by means of the drain 12. A spring loaded injection valve 13 opens when the pressure in the pumps 9 is greater than the pressure in the extruder. The valve 13 is shown in the closed position. When the valve opens, the valve head enters into the screw flight cutout 14. The molten polyethylene terephthalate and ethylene glycol are mixed in the in-line mixer 5 to aid reduction of the molecular weight of the polyethylene terephthalate. Temperature in the extruder is in the range of 280° C. to 285° C. while pressure is about 1000 psi. The total residence time of the ethylene glycol and polyethylene terephthalate in the pre-molecular weight reduction zone is about two minutes. The lower molecular weight polyethylene terephthalate is then passed via pipe 15 to a hydrolyzer, not shown. The hydrolyzer may be operated, for example, as described in U.S. application Ser. No. 263,812 filed Dec. 21, 1983, the disclosure of which is incorporated herein by reference. In the hydrolyzer, the molten lower molecular weight polyethylene terephthalate is contacted with water at a high temperature to depolymerize the polymer to ethylene glycol and terephthalic acid. The hydrolyzer is operated at a pressure of about 600 psi. The hydrolysis reaction is complete in about 15 minutes. In contrast, as shown in FIG. 2, when polyethylene terephthalate is fed to the hydrolysis chamber operated at 600 psi without subjecting it to pre-glycolysis, about 45 minutes is required to complete the hydrolysis reaction. Further, as shown in FIG. 2, even when the pressure in the hydrolyzer is increased to 800 psi, 30 minutes is required to complete hydrolysis where the polyethylene terephthalate has not been subjected to pre-glycolysis.

EXAMPLE 2

When the process of Example 1 is repeated using as the feed material to the extruder polybutylene terephthalate instead of the polyethylene terephthalate used in Example 1 and substituting 1,4-butanediol for the ethylene glycol used in Example 1, there are recovered from the hydrolyzer complete depolymerization products consisting of terephthalate acid crystals, tetrahydrofuran and 1,4-butanediol.

EXAMPLE 3

When the process of Example 1 is repeated substituting nylon 6 for the polyethylene terephthalate used in Example 1 and substituting caprolactam for the ethylene glycol used in Example 1, there is obtained from the hydrolyzer caprolactam.

EXAMPLE 4

When the process of Example 1 is repeated substituting nylon 66 waste material for the polyethylene terephthalate waste material used in Example 1 and substituting hexamethylenediamine for the ethylene glycol used in Example 1, there are produced as hydrolysis products in the hydrolyzer hexamethylenediamine and adipic acid.

The invention has been described in considerable detail with particular reference to certain preferred embodiments thereof. However, variations and modifications can be effected within the spirit and scope of the invention as described hereinbefore, and as defined in the appended claims.

What is claimed is:

1. A process for the depolymerization of a condensation polymer comprising the steps in combination:
   (a) intimately admixing molten condensation polymer selected from the group consisting of polyamides and polyesters with a depolymerization agent selected from the group consisting of (i) a product resulting from the complete hydrolytic depolymerization of said condensation polymer in liquid form, and (ii) water, said depolymerization agent being present in said admixture in an amount by weight of less than the weight of said condensation polymer,
   (b) admixing said molten condensation polymer and said depolymerization agent for a time sufficient that the molecular weight of said condensation polymer is reduced by at least 50%; and
   (c) subjecting said treated condensation polymer to neutral hdryolysis with a substantial excess of water based on the weight of the condensation polymer, to thereby effect substantially complete hydrolytic depolymerization of said condensation polymer.

2. The process defined in claim 1 wherein said condensation polymer is intimately admixed with said depolymerization agent at a temperature of greater than about 10° C. above the melting temperature of the condensation polymer.

3. The process defined in claim 2 wherein said temperature is greater than about 20° C. above the melting point of the condensation polymer.

4. The process defined in claim 2 wherein the depolymerization agent is a product resulting from the complete hydrolytic depolymerization of the condensation polymer.

5. The process defined in claim 3 wherein the depolymerization agent is a product resulting from the complete hydrolytic depolymerization of the condensation polymer.

6. The process defined in claim 4 wherein the condensation polymer is a polyester and the depolymerization product is a dihydric alcohol.

7. The process defined in claim 6 wherein said polyester is treated with said dihydric alcohol as the depolymerization agent at a temperature of from 260°-310° C.

8. The process defined in claim 7 wherein said treatment is conducted at a pressure of from 500-2,000 psi.

9. The process defined in claim 8 wherein said polyester is polyethylene terephthalate and said depolymerizing agent is ethylene glycol.

10. The process defined in claim 8 wherein said polyester is butylene terephthalate and said depolymerization agent is 1,4-butanediol.

11. The process defined in claim 4 wherein said condensation polymer is a polyamide.

12. The process defined in claim 11 wherein said polyamide is nylon 6 and said depolymerization agent is caprolactam.

13. The process defined in claim 11 wherein said polyamide is nylon 66 and said depolymerization agent is hexamethylenediamine.

14. The process defined in claim 4 wherein the depolymerization agent is present in an amount of less than about 25% by weight, based on the weight of the condensation polymer.

15. The process defined in claim 14 wherein said depolymerization agent is present in an amount of less than about 10% by weight, based on the weight of the condensation polymer.

16. The process defined in claim 15 wherein said temperature is greater than about 20° C. above the melting point of the condensation polymer.

17. The process defined in claim 4 wherein the total time resulting from said steps (a), (b) and (c) is less than one-half the total time which would be required to effect substantially complete hydrolysis of the condensation polymer using step (c), alone.

18. A process for the depolymerization of a condensation polymer comprising steps in combination:
   (a) intimately admixing in a high temperature and high pressure screw extruder under high shear conditions, a molten condensation polymer selected from the group consisting of polyamides and polyesters with a depolymerization agent comprising at least one of the products resulting from complete hydrolytic depolymerization of said condensation polymer in liquid form, said depolymerization agent being present in said admixture in an amount by weight of less than the weight of said condensation polymer, said admixture forming a homogenous mass,
   (b) admixing said molten condensation polymer and said depolymerization agent while passing said mixture through the barrel of said screw extruder for a time sufficient that the molecular weight of said condensation polymer is reduced by at least 50%; and
   (c) subjecting said treated condensation polymer to neutral aqueous hydrolysis with a substantial excess of water based on the weight of the condensation polymer, at a pressure of less than the pressure in said extruder, to thereby effect substantially complete hydrolytic depolymerization of said condensation.

19. The process defined in claim 18 wherein said depolymerization agent is admitted to said extruder through a valve situated such that its outlet discharges into the barrel of the extruder.

20. The process defined in claim 19 wherein said intimate admixture is passed through a static mixer, in-line with said extruder, and downstream of said valve, and upstream of the hydrolysis zone.

21. The process defined in claim 18 wherein the temperature in said extruder is at least 10° above the melting point of the condensation polymer.

22. The process defined in claim 21 wherein the temperature in the extruder is at least 20° C. above the melting temperature of the condensation polymer.

23. The process defined in claim 21 wherein the depolymerization agent is present in an amount of less than about 25% by weight, based on the weight of the polymer.

24. The process defined in claim 23 wherein the depolymerization agent is present in an amount of less than about 10%, by weight, based on the weight of the condensation polymer.

25. The process defined in claim 24 wherein the condensation polymer is a polyester and the depolymerization agent is a dihydric alcohol.

* * * * *